United States Patent [19]

Wang et al.

[11] Patent Number: 5,436,363

[45] Date of Patent: Jul. 25, 1995

[54] METHOD FOR MAKING ALKYL-α-CYANOACRYLATE FROM DEPOLYMERIZATION OF POLY(ALKYL-α-CYANOACRYLATE)

[75] Inventors: Tien-Lu Wang; Tso-Chi Chiu; Kun-Chuo Chen, all of Hsinchu, Taiwan

[73] Assignee: Industrial Technology Research Institute, Chutung, Taiwan

[21] Appl. No.: 315,998

[22] Filed: Oct. 3, 1994

[51] Int. Cl.$^6$ .......................................... C07C 253/30
[52] U.S. Cl. ...................................... 558/381; 558/372
[58] Field of Search .............................. 558/381, 372

[56] References Cited

U.S. PATENT DOCUMENTS

| | | | |
|---|---|---|---|
| 2,756,251 | 7/1956 | Joyner et al. | 558/381 |
| 3,254,111 | 5/1966 | Hawkins et al. | 558/381 |
| 3,444,233 | 5/1969 | Rabinowitz | 558/372 X |
| 3,465,027 | 9/1969 | Hawkins | 558/381 |
| 3,728,373 | 4/1973 | Mohel et al. | 558/381 |
| 3,751,445 | 8/1973 | Imoehl et al. | 558/381 |
| 4,328,170 | 5/1982 | Okawara et al. | 558/372 |

FOREIGN PATENT DOCUMENTS

| | | | |
|---|---|---|---|
| 2738285 | 3/1979 | Germany | 558/372 |
| 57-116037 | 7/1982 | Japan | 558/372 |
| 932328 | 7/1963 | United Kingdom | 558/372 |
| 1130638 | 10/1968 | United Kingdom | 558/372 |

*Primary Examiner*—Joseph Paul Brust
*Attorney, Agent, or Firm*—W. Wayne Lianh

[57] ABSTRACT

A depolymerization and purification process, by which a poly(alkyl-α-cyanoacrylate) feed is depolymerized into high-purity cyanoacrylate monomers without the use of a high-boiling heat transfer medium such as tricresyl phosphate. The poly(alkyl-α-cyanoacrylate) feed, which contains one or more polymerization inhibitors such as hydroquinone and phosphorus pentoxide, is first introduced into a thin-film evaporator for a depolymerization reaction. The temperature of the film evaporator is maintained at about 200°~260° C., and operated under a vacuum of 1~20 mm Hg. The produced gas stream from the depolymerization reactor is subject to a two-stage heat transfer process for condensation and purification. The first stage involves a very-high temperature condenser (about 150° C.). The residue collected in the first stage condenser contains primarily dimers of α-cyanoacrylate. The second stage involves a conventional condenser at room temperature or lower temperature. The gaseous stream leaving the intermediate very-high temperature condenser contains primarily the desired cyanoacrylate monomer, thus it can be conveniently condensed in a conventional condenser, and the product is a very high purity cyanoacrylate product. This process eliminates the need of using a high-boiling heat transfer medium, thus eliminating the production of liquid waste, while allowing high-yield and high-purity final product of cyanoacrylate monomers to be produced in a continuous manner.

14 Claims, 1 Drawing Sheet

METHOD FOR MAKING ALKYL-α-CYANOACRYLATE FROM DEPOLYMERIZATION OF POLY(ALKYL-α-CYANOACRYLATE)

FIELD OF THE INVENTION

This invention relates to an improved method for making alkyl-α-cyanoacrylate. More specifically, this invention relates to an improved method for making high-purity alkyl-α-cyanoacrylate by the depolymerization of poly(alkyl-α-cyanoacrylate). The method disclosed in the present invention allows high-purity alkyl-α-cyanoacrylate to be made from poly(alkyl-α-cyanoacrylate) in a continuous manner with minimum reaction wastes.

BACKGROUND OF THE INVENTION

Alkyl-α-cyanoacrylate is one of the most commonly used "instant" adhesives. Conventionally, alkyl-α-cyanoacrylate is prepared using alkyl-α-cyanoacetate and formaldehyde as raw materials, which are reacted under an alkalinic environment to form poly(alkyl-α-cyanoacrylate). The poly(alkyl-α-cyanoacrylate) is then cracked (i.e., depolymerized) and purified to obtain high-purity alkyl-α-cyanoacrylate.

U.S. Pat. No. 2,756,251 discloses a method for the preparation of monomeric α-cyanoacrylate by which a polymeric ester of α-cyanoacrylic acid is heated in a tertiary ester of phosphoric acid, for example tricresyl phosphate, at a temperature above the melting point of the polymer to produce the monomeric α-cyanoacrylate. The amount of tricresyl phosphate required in the process disclosed in the '251 patent is about 0.9 times that of the polymeric raw material. The reaction is conducted as a batch process. Because of the high viscosity of the reaction mixture, very slow depolymerization rate is experienced. Typically, it takes between 5 and 10 hours to complete the reaction. The reaction time will be substantially prolonged if inadequate mixing is provided. When the reactant polymer is subject to long time exposure in the high-temperature (typically about 200° C.) environment, it property will deteriorate causing the reaction yield to be adversely affected. Furthermore, large amounts of dark brownish residue will be produced after the depolymerization reaction. This causes significant difficulty in cleaning the reactor which also indirectly results in reduced production capacity.

U.S. Pat. No. 3,728,373 discloses a continuous method for making cyanoacrylic acid esters by depolymerization polycyanoacrylic acid esters. The polymer is first admixed with an inert liquid of high boiling point, such as tricresyl phosphate, and one or more polymerization inhibitors, such as phosphorus oxide and hydroquinone. Then the mixture is depolymerized by heating a thin layer of this mixture to produce high-purity monomeric α-cyanoacrylate gas. The monomeric α-cyanoacrylate gas is then condensed at −8° C. to form the final product. The continuous process disclosed in the '373 patent is a substantially improved process over that disclosed in the '251 patent. However, it requires the use of large amounts of tricresyl phosphate (1.45 times the amount of the polycyanoacrylic acid esters), thus resulting in serious liquid pollution and disposal problems.

SUMMARY OF THE INVENTION

The primary object of the present invention is to develop a process for the production of alkyl-α-cyanoacrylate which minimizes the production of reaction waste. More specifically, the primary object of the present invention is to develop a process, which utilizes a thin-layer evaporator in a continuous manner for the production of high-purity alkyl-α-cyanoacrylate and which does not require the use of a high boiling point heat transfer medium, such as the tricresyl phosphate typically used in the prior art, so as to minimize the amount of unwanted waste that will be generated if such high boiling point heat transfer medium is used.

Prior art processes for making alkyl-α-cyanoacrylate always require the use of high-boiling-point tricresyl phosphate or its equivalent, which is admixed with poly(alkyl-α-cyanoacrylate) to serve as a heat transfer medium, in order to produce high purity monomeric alkyl-α-cyanoacrylate. In the present invention, it was discovered that unexpected results were obtained that, when a high-temperature (at about 150° C.) intermediate condenser was used after the thin-layer evaporator but before the final condenser, high-purity cyanoacrylate can be produced without incurring the disadvantages experienced in the prior art processes. The co-inventors have discovered that, by utilizing the high-temperature intermediate condenser, the requirement of using tricresyl phosphate as a heat transfer medium can be eliminated, thus greatly reducing the amount of reaction waste. The process of producing high-purity cyanoacrylate monomers as disclosed in the present invention can be conducted in a continuous manner.

In the process disclosed in the present invention, a poly(alkyl-α-cyanoacrylate) feed without a high-boiling heat transfer medium is first introduced into a thin-film evaporator for a depolymerization reaction. The produced gas is then subject to a two-stage heat transfer process for condensation and purification. The first stage involves a very high temperature condenser (about 150° C.). The residue collected during the first stage condenser contains primarily dimers of α-cyanoacrylate. One of the advantages of using such a very-high temperature intermediate condenser is to eliminate the need of using a high-boiling heat transfer medium while allowing high-yield and high-purity final product of cyanoacrylate monomers to be obtained.

Typically, the gaseous components produced from the depolymerization reactor are subject to a conventional condenser at low temperature. In order to ensure high purity of the final product, the feed in the prior art processes always contains a high-boiling solvent, such as tricresyl phosphate, so as to retain the amount of undesired byproducts such as dimers in the liquid residue and minimize the amount of impurities in the produced gas stream. In the present invention, the gaseous stream from the intermediate very-high temperature condenser contains primarily only the desired cyanoacrylate monomer, thus it can be conveniently condensed in a conventional condenser, and the product is a high purity cyanoacrylate product.

BRIEF DESCRIPTION OF THE DRAWING

The present invention will be described in detail with reference to the drawing showing the preferred embodiment of the present invention, wherein.

DETAILED DESCRIPTION OF THE PREFERRED EMBODIMENT

Figure 1:
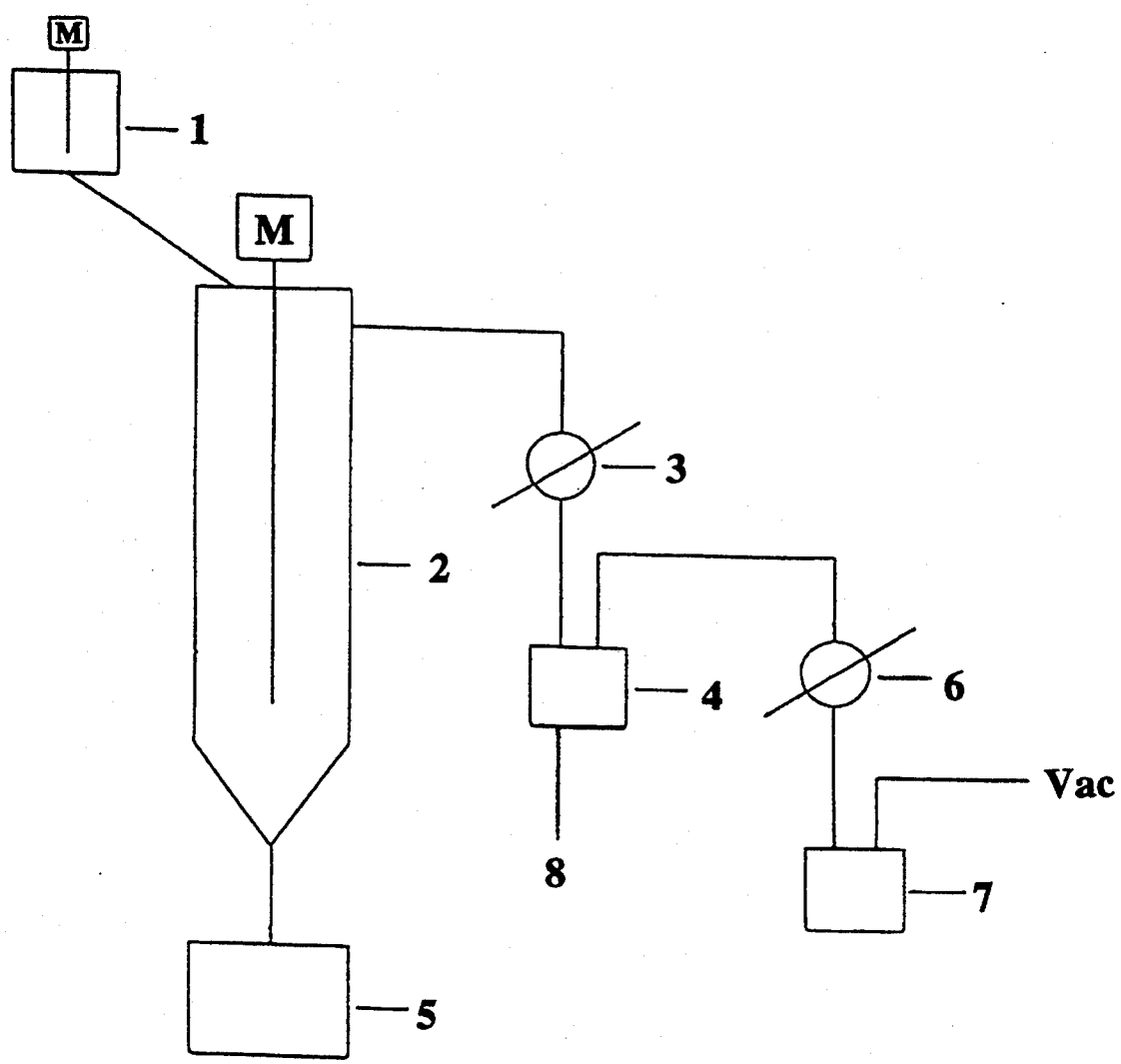
FIG. 1 is a schematic drawing showing the process disclosed in the present invention for the production of high purity cyanoacrylate monomer from a poly(alkyl-α-cyanoacrylate) feed via a depolymerization reaction without the use of a heat transfer medium such as tricresyl phosphate.

The present invention discloses a depolymerization/purification process, by which a poly(alkyl-α-cyanoacrylate) feed is depolymerized into high-purity cyanoacrylate monomers without using a high-boiling heat transfer medium such as tricresyl phosphate. The poly(alkyl-α-cyanoacrylate) feed is first introduced into a thin-film evaporator for a depolymerization reaction. The temperature of the film evaporator was maintained at about 200°~260° C., and operated under a vacuum of 1~20 mm Hg. The produced gas stream from the depolymerization reactor is subject to a two-stage heat transfer process for condensation and purification. The first stage involves a very high temperature condenser (about 150° C.). The residue collected in the first stage condenser contains primarily dimers of α-cyanoacrylate. The second stage involves a conventional condenser at room temperature or lower. In the present invention, the gaseous stream leaving the intermediate very-high temperature condenser contains primarily only the desired cyanoacrylate monomer, thus it can be conveniently condensed in a conventional condenser, and the product is a high purity cyanoacrylate product.

The present invention will now be described more specifically with reference to the following examples. It is to be noted that the following descriptions of example including preferred embodiment of this invention are presented herein for purpose of illustration and description; it is not intended to be exhaustive or to limit the invention to the precise form disclosed.

EXAMPLE 1

As shown in FIG. 1, which is a schematic drawing showing the main steps of the process disclosed in the present invention, a reactant mixture, which contained 1 kg of poly(alkyl-α-cyanoacrylate), 4 g of hydroquinone and 12 g of phosphorus pentoxide, was mixed in a mixer 1. The reaction mixture was continuously fed, at a rate of 5 g/min, into a film evaporator 2, in which the poly(alkyl-α-cyanoacrylate) feed was subject to a depolymerization reaction. The film evaporator 2 has a dimension of 5 cm in diameter and 60 cm in length. Heat provided to the film evaporator 2, which was operated at a 10 mm Hg vacuum, was through a heat transfer medium at 220° C. The depolymerization was very complete. After the depolymerization reaction in the film evaporator, the gas stream, which contained cyanoacrylate monomers and higher-boiling residues, was introduced into an intermediate heat exchanger 3. The liquid stream from depolymerization reactor was collected in a collector 5, at a rate of 0.25 g/min. This represented a reaction yield of 95%. The temperature of the intermediate heat exchanger 3 was maintained at about 150° C. The higher-boiling residue 8 in the gas stream was collected as a liquid product in the liquid collector 4, at a rate of 1.5 g/min. The gaseous stream from the liquid collector 4 was entered into a second heat exchanger 6, which was maintained at room temperature. The liquid product was collected in a final liquid collector 7. 3.25 g/min of very high purity ethyl-α-cyanoacrylate was collected in the final liquid collector 7, representing an overall yield of 65%.

EXAMPLE 2

Similar to the steps described in Example 1, a reactant mixture, which contained 4 kg of poly(alkyl-α-cyanoacrylate), 16 g of hydroquinone, and 48 g of phosphorus pentoxide, was mixed in a mixer 1 and continuously fed, at a rate of 33 g/min, into a film evaporator 2, in which the poly(alkyl-α-cyanoacrylate) feed was subject to a depolymerization reaction. The film evaporator 2 has a dimension of 32 cm in diameter and 49 cm in length. Heat provided to the film evaporator 2, which was operated at a 10 mm Hg vacuum, was through a heat transfer medium at 220° C. The depolymerization was very complete. After the depolymerization reaction in the film evaporator, the gas stream, which contained cyanoacrylate monomers and higher-boiling residues, was introduced into an intermediate heat exchanger 3. The liquid stream from depolymerization reactor was collected in a collector 5, at a rate of 1.65 g/min. This represented a reaction yield of 95%. The temperature of the intermediate heat exchanger 3 was maintained at about 150° C. The higher-boiling residue 8 was collected as a liquid product in the liquid collector 4, at a rate of 10.6 g/min. The gaseous stream from the liquid collector 4 was entered into a second heat exchanger 6, which was maintained at room temperature. The liquid product was collected in a final liquid collector 7. 20.8 g/min of very high purity ethyl-α-cyanoacrylate was collected in the final liquid collector 7, representing an overall yield of 63%.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A method for making alkyl-α-cyanoacrylate comprising the steps of:
   (a) preparing a reaction mixture comprising poly(alkyl-α-cyanoacrylate) and a polymerization inhibitor;
   (b) introducing said reaction mixture into a thin-layer evaporator at about 200° to 260° C. to form a first gas stream and a first residual stream;
   (c) subjecting said first gas stream to a first heat exchanger at 120° to 170° C. and forming a second gas stream and a second residual stream; and
   (d) condensing said second gas stream in a condenser to form said alkyl-α-cyanoacrylate.

2. The method for making alkyl-α-cyanoacrylate according to claim 1 wherein said polymerization inhibitor is hydroquinone, phosphorus pentoxide, or a mixture thereof.

3. The method for making alkyl-α-cyanoacrylate according to claim 1 wherein said step (b) is operated at 220° C.

4. The method for making alkyl-α-cyanoacrylate according to claim 1 wherein said step (c) is operated at 150° C.

5. The method for making alkyl-α-cyanoacrylate according to claim 1 wherein said thin-layer evaporator in step (b) is operated at 10 mm Hg vacuum.

6. The method for making alkyl-α-cyanoacrylate according to claim 1 wherein said alkyl-α-cyanoacrylate is ethyl-α-cyanoacrylate, and said poly(alkyl-α-cyanoacrylate) is poly(ethyl-α-cyanoacrylate).

7. A method for making alkyl-α-cyanoacrylate comprising the steps of:
 (a) preparing a reaction mixture consisting essentially of poly(alkyl-α-cyanoacrylate) and a polymerization inhibitor;
 (b) introducing said reaction mixture into a thin-layer evaporator at about 200° to 260° C. to form a first gas stream and a first residual stream;
 (c) subjecting said first gas stream to a first heat exchanger at 120° to 170° C. and forming a second gas stream and a second residual stream; and
 (d) condensing said second gas stream in a condenser to form said alkyl-α-cyanoacrylate.

8. The method for making alkyl-α-cyanoacrylate according to claim 7 wherein said polymerization inhibitor is hydroquinone, phosphorus pentoxide, a mixture thereof.

9. The method for making alkyl-α-cyanoacrylate according to claim 7 wherein said step (b) is operated at 220° C.

10. The method for making alkyl-α-cyanoacrylate according to claim 7 wherein said step (c) is operated at 150° C.

11. The method for making alkyl-α-cyanoacrylate according to claim 7 wherein said thin-layer evaporator in step (b) is operated at 10 mm Hg vacuum.

12. The method for making alkyl-α-cyanoacrylate according to claim 7 wherein said alkyl-α-cyanoacrylate is ethyl-α-cyanoacrylate, and said poly(alkyl-α-cyanoacrylate) is poly(ethyl-α-cyanoacrylate).

13. A method for making alkyl-α-cyanoacrylate comprising the steps of:
 (a) preparing a reaction mixture which contains poly(alkyl-α-cyanoacrylate) and a polymerization inhibitor;
 (b) introducing said reaction mixture into a thin-layer evaporator at about 200° to 260° C. to form a first gas stream and a first residual stream;
 (c) subjecting said first gas stream to a high temperature consensor operating at 120° to 170° C. and forming a second gas stream and a second residual stream; and
 (d) condensing said second gas stream in a cold condenser operating at room temperature to collect said alkyl-α-cyanoacrylate.

14. A method for making alkyl-α-cyanoacrylate according to claim 13 wherein said reaction mixture in step (a) does not contain tricresyl phosphate.

* * * * *